United States Patent
Smith, Jr. et al.

(10) Patent No.: US 10,357,197 B2
(45) Date of Patent: Jul. 23, 2019

(54) SYSTEM AND METHOD FOR MONITORING A PERSON VIA AN ANALOG MULTI-ZONE PRESSURE SENSITIVE PAD

(71) Applicant: J. BRASCH CO., LLC, Lincoln, NE (US)

(72) Inventors: Gordon Smith, Jr., Lincoln, NE (US); John Joseph Brasch, Lincoln, NE (US); James R Leacock, Lincoln, NE (US); Yuanjian Li, Chengdu (CN)

(73) Assignee: J. Brasch Co., LLC, Lincoln, NE (US)

( * ) Notice: Subject to any disclaimer, the term of this patent is extended or adjusted under 35 U.S.C. 154(b) by 0 days.

(21) Appl. No.: 15/574,479

(22) PCT Filed: May 16, 2016

(86) PCT No.: PCT/IB2016/052835
§ 371 (c)(1),
(2) Date: Nov. 15, 2017

(87) PCT Pub. No.: WO2016/185364
PCT Pub. Date: Nov. 24, 2016

(65) Prior Publication Data
US 2018/0125413 A1     May 10, 2018

Related U.S. Application Data

(60) Provisional application No. 62/161,903, filed on May 15, 2015, provisional application No. 62/307,774, filed on Mar. 14, 2016.

(51) Int. Cl.
*A61B 5/00* (2006.01)
*G08B 21/22* (2006.01)
(Continued)

(52) U.S. Cl.
CPC .............. *A61B 5/447* (2013.01); *A61B 5/00* (2013.01); *A61B 5/6891* (2013.01);
(Continued)

(58) Field of Classification Search
CPC .. A61G 7/0527; A61G 7/057; A61G 7/05769; A61G 7/108;
(Continued)

(56) References Cited

U.S. PATENT DOCUMENTS

| | | | | |
|---|---|---|---|---|
| 5,962,118 A | * | 10/1999 | Burgess | ................ H01H 1/029 252/503 |
| 2002/0067273 A1 | * | 6/2002 | Jaques | .................... A61B 5/11 340/573.4 |

(Continued)

*Primary Examiner* — Orlando Bousono
(74) *Attorney, Agent, or Firm* — Michael D. Eisenberg

(57) ABSTRACT

A pressure sensitive pad, generally planar in shape for placement underneath a mattress or cushion, capable of outputting a spectrum of signals depending on the pressure applied on the pad, comprising a plurality of sensitive zones, each zone being connected to a respective controller, configured to measure the pressure on each zone. The pressure sensitive pad comprising two electrically conductive layers; a variable conductive foam layer between the two conductive layers; and a non-conductive layer comprising a plurality of holes, disposed between a first of the two electrically conductive layers and the conductive foam layer. A system operable with the pad calibrates to detect absence and presence of a person for a range of mattress types and mattress weights and person weights; and determines a relative weight and position of the person while the person is on the mattress.

18 Claims, 9 Drawing Sheets

(51) Int. Cl.
*A61G 7/10* (2006.01)
*A61G 7/057* (2006.01)
*A61G 7/05* (2006.01)

(52) U.S. Cl.
CPC ............ *A61B 5/6892* (2013.01); *A61G 7/057* (2013.01); *A61G 7/108* (2013.01); *G08B 21/22* (2013.01); *A61B 5/445* (2013.01); *A61B 2562/0247* (2013.01); *A61B 2562/06* (2013.01); *A61B 2562/066* (2013.01); *A61G 7/0527* (2016.11); *A61G 2203/34* (2013.01); *A61G 2203/44* (2013.01)

(58) Field of Classification Search
CPC ............ A61G 2203/34–44; A61B 5/00; A61B 5/445; A61B 5/447; A61B 5/6891–6892; A61B 5/024; A61B 2562/046; A47C 27/083
See application file for complete search history.

(56) References Cited

U.S. PATENT DOCUMENTS

| | | | |
|---|---|---|---|
| 2004/0194220 A1* | 10/2004 | Price | A61B 5/0205 5/713 |
| 2005/0273940 A1* | 12/2005 | Petrosenko | A61B 5/1126 5/722 |
| 2006/0075559 A1* | 4/2006 | Skinner | A61G 7/05769 5/615 |
| 2006/0244466 A1* | 11/2006 | Call | A61B 5/6887 324/661 |
| 2008/0060138 A1* | 3/2008 | Price | A61B 5/0205 5/713 |
| 2009/0144909 A1* | 6/2009 | Skinner | A61G 7/05776 5/713 |
| 2009/0183312 A1* | 7/2009 | Price | A61B 5/0205 5/706 |
| 2009/0270770 A1* | 10/2009 | Petrosenko | A61B 5/1126 600/595 |
| 2011/0209287 A1* | 9/2011 | Call | A61B 5/6887 5/658 |
| 2013/0019406 A1* | 1/2013 | Riley | A61B 5/0816 5/600 |
| 2013/0283530 A1* | 10/2013 | Main | A47C 31/12 5/600 |
| 2014/0039351 A1* | 2/2014 | Mix | A61B 5/1114 600/587 |
| 2014/0059781 A1* | 3/2014 | Lafleche | A47C 27/083 5/713 |

\* cited by examiner

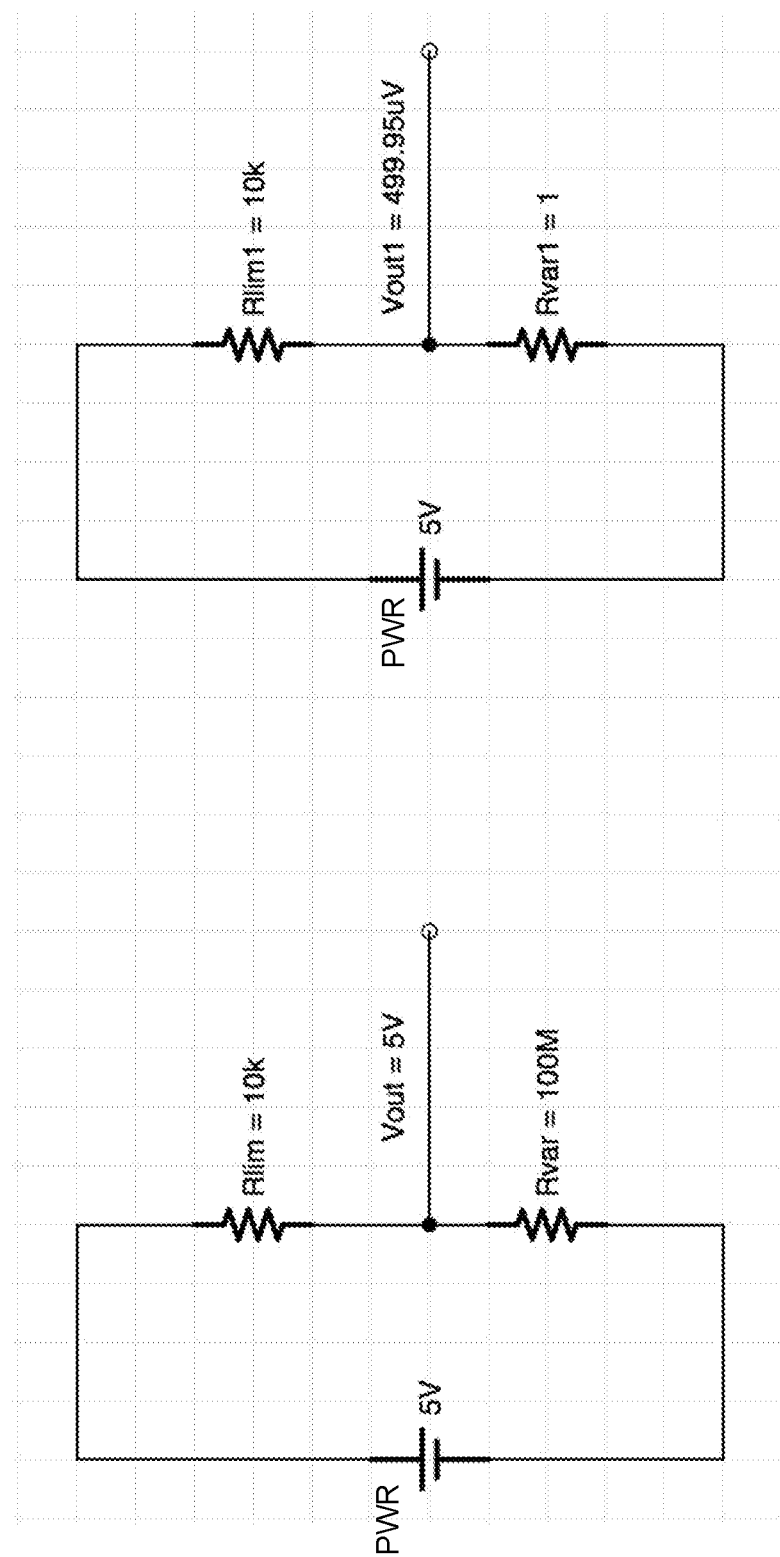

SYSTEM AND METHOD FOR MONITORING A PERSON VIA AN ANALOG MULTI-ZONE PRESSURE SENSITIVE PAD

CROSS-REFERENCES TO RELATED APPLICATIONS

The present application claims priority from U.S. Provisional Application Ser. No. 62/161,903 filed on May 15, 2015 and U.S. Provisional Application Ser. No. 62/307,774 filed on Mar. 14, 2016, both of which are hereby incorporated herein by reference in their respective entirety.

BACKGROUND OF INVENTION

Pressure pads are used in the medical field to sense the presence of a monitored person on a surface, like a chair or a bed.

Pressure pads may be used under the mattress/cushion or on the mattress/cushion. Pressure pads located on the mattress can be exposed to bodily fluids. It is sometimes also a concern to nurse managers because of possible subtle changes in pressure on the skin, leading to decubitus ulcers.

The inventors have found that pressure switch pads known in the industry are not very reliable when used under a mattress/cushion. Variations in thickness, softness, and internal structure of the mattress/cushion result in sporadic behavior, which results in unreliable detection of the presence or absence of monitored person. One reason for this lies in the fact that basic pressure pads are created to have a specific force sensitivity, which has to be carefully selected. If the pressure pad is too sensitive, the mattress/cushion alone could trigger the pad. If the pressure pad is too lenient, the pad may not detect the presence of a light person. This is further complicated by the fact that different models of mattresses have varying masses and distributing the weight of an individual over different areas.

BRIEF SUMMARY OF THE INVENTION

To solve the above problem, the present invention makes use of an analog pressure pad, which can measure a wide range of pressures and convey data instead of a simple on/off switch. This data can then be read by a controller and processed, for example by evaluated over time and/or being compared on previous readings. This processing enables automatic calibration of the same analog pressure pad for different types of mattresses and different weights of users. In this manner, the presence of a user on a bed can be detected for a wide range of mattress/cushion types and weights and for a wide range of users. In some embodiments of the present invention, the pressure pad has a tare (relative weight) function, for allowing the monitor connected to the pressure pad to take into account the weight of the mattress/cushion in use and subtract that weight from a calculated total to get a weight measurement of the user.

In other embodiments of the present invention, the controller is configured for periodically taking automatic measurements from the pad, and averaging them over an inactive time period (i.e., a time in which it is known that the person is not on the mattress) to auto calibrate the tare weight. This, combined with some intelligent thresholds, could account for weight differences due to changes in bedding, pillows, etc. over time.

This solution has the added benefit of being able to produce a relative weight measurement of an individual simply by them going to bed during the day or for the night. Relative weight measurements could be used to detect weight gain or loss of the user over time and possibly, if calibrated correctly, supply an actual weight measurement (pounds, kilograms, etc). Historical relative weight measurements could also aid in the detection of pets which might jump into bed, such as a dog, which might otherwise have triggered a basic pressure pad.

It should be noted that the pad of the present invention may be used under any kind of mattress cushion. In the following sections of the document, the term "mattress" is meant to include any kind of mattress, cushion, or support on which a person may sit or lie.

(1) In a variant, a pressure sensitive pad is generally planar in shape for placement underneath a mattress or cushion, and is capable of outputting a spectrum of signals depending on the pressure applied on the pad.

(2) In another variant, the pressure sensitive pad is configured for substantially not deforming the mattress or cushion.

(3) In a further variant, the pressure sensitive pad comprises at least one of: a conductive film; a conductive foam; a conductive ink; and a strain gauge.

(4) In still another variant, the pressure sensitive pad comprises a plurality of sensitive zones, each zone being connected to a respective controller, configured to measure the pressure on each zone.

(5) In yet a further variant, the pressure sensitive pad comprises two electrically conductive layers. A variable conductive layer is disposed between the two conductive layers, configured such that a resistance of the variable conductive layer decreases when pressure is applied on the variable conductive layer and the variable conductive layer is compressed. The two electrically conductive layers are separated by the variable conductive layer, such that the electrical resistance between the two conducting layers decreases as pressure is applied to the pad, by way of increasing electrical conductivity between the two conducting layers as mechanical pressure increases on the pad and the variable conductive layer is compressed.

(6) In a variant of the pressure sensitive pad, the variable conductive layer is a conductive foam layer.

(7) In another variant, the pressure sensitive pad comprises a non-conductive layer comprising a plurality of holes, disposed between a first of the two electrically conductive layers and the conductive foam layer. Pressure applied to the pad increases contact between the first conductive layer and the conductive foam, thereby easing electrical conductivity between the two electrically conductive layers.

(8) In a further variant, the pressure sensitive pad comprises a controller connected to the two conducting layers and configured to input a signal that passes through the two electrically conductive layers to read an output signal resulting from the input signal passing through the electrically conductive layers; and two sheath layers that contain and protect the electrically conductive layers.

(9) In still another variant, s system for detecting weight of a person or weight changes over time or movements of a person on a mattress, comprises: an analog pressure sensitive pad; and a control unit configured for processing data received from the pad, and the control unit operable to: (a) calibrate the system to detect absence and presence of a person for a range of mattress types and mattress weights and person weights; and (b) determine a relative weight of the person while the person is on the mattress.

(10) In yet a further variant of the system, the control is operable to: (c) send processed data to a remote system; (d)

emit an alarm if an undesirable situation concerning the person's presence/absence occurs; and (e) stop the alarm if a certain input is received.

(11) In a variant of the system, the pressure sensitive pad is a variable pressure sensitive pad configured for placement under a mattress.

(12) In another variant, the system comprises a local output unit configured for emitting an alarm in response to an undesirable condition of the person occurring based on information from the pad.

(13) In a further variant, the system comprises a local input configured for receiving a termination signal, communicated to the controller, whereby the controller if configured to terminate an emitted alarm.

(14) In still another variant, the system comprises a remote communication unit configured to transmit data processed by the control unit to a remote system.

(15) In yet a further variant of the system, the data transmitted is alert data.

(16) In another variant of the system, the data is weight data.

(17) In a variant, a method for calibrating a variable pressure sensitive pad to detect a person's weight with the analog pressure sensitive pad placed beneath a mattress of an unknown weight and the person is on the mattress, the calibration comprising: a) placing the pressure variable pressure sensitive pad undress a mattress; b) measuring a high, a low, a last reading and an average reading from the pad; c) if the difference is smaller than a threshold, gathering more data until threshold is passed; d) if the difference is greater than the threshold: determining a deactivated zone, wherein the deactivated zone is a range of values from the high to a value that is a function of the low and high; determining an activated zone, wherein the activated zone is a range of values from the low to a value that is a second function of the low and high; and determining a transition zone, wherein the transition zone is range between the highest value of the activated zone and the lowest of deactivated zone; e) if the average value is in the transitioning region, then performing an iterative process of lowering the record high by a second amount that is a third function of the previous record highs and lows and increasing the record low by a third amount that is a fourth function of the previous record highs and lows, until the last reading is out of the transitioning region.

(18) In another variant of the method, the second amount and the third amount are equal to each other.

(19) In a further variant, a method for determining a person's relative weight using the pressure sensitive pad, on a mattress of unknown weight, while the pad is beneath the mattress of an unknown weight and the person is on the mattress, comprises measuring an output voltage of the pad and determining the relative weight of the person based on the output voltage.

(20) In still another variant, the method for determining the movement of a person on a mattress, using the pressure sensitive pad under the mattress, comprises comparing measurements of an output from each of the sensitive zones over time and determining whether an output from a first zone is higher than an adjacent zone over time.

BRIEF DESCRIPTION OF DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIGS. 5 and 6 are schematic drawings of an electrical circuit which includes the pad of FIGS. 3 and 4, according to some embodiments of the present invention;

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
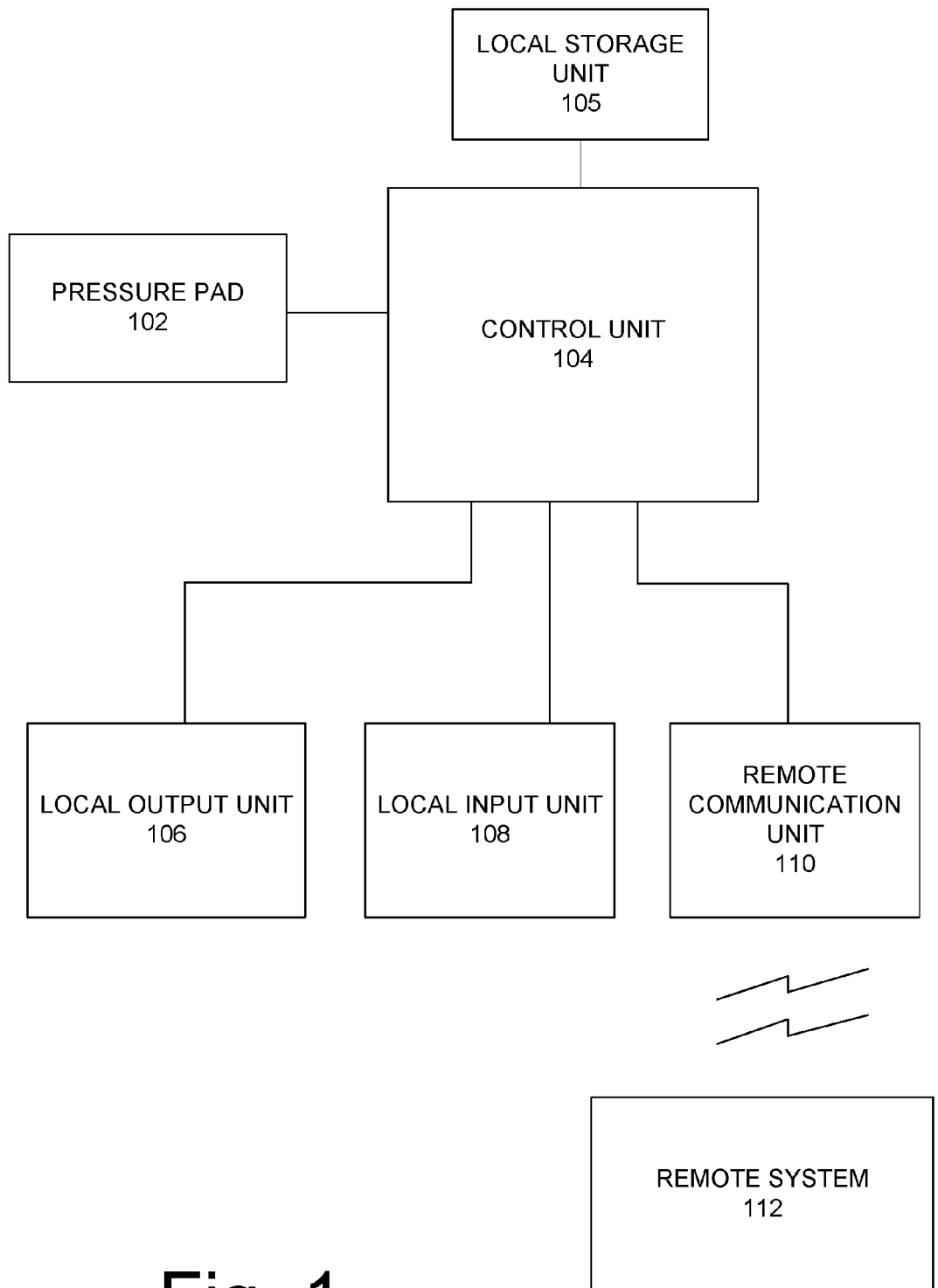
FIG. 1 is a block diagram illustrating a monitoring apparatus comprising an analog pad, according to some embodiments of the present invention.

FIG. 1 is a box diagram illustrating a monitoring apparatus according to some embodiments of the present invention. The monitoring apparatus includes a pressure pad 102, and a control unit 104. Optionally, the control unit is in communication with a local memory unit 105, for storing data received from the pressure pad, or uses a remote communication unit 110 to transfer data to a remote system 112, which is configured for storing and/or analyzing the received data. Optionally, the system includes a local output unit 106 and a local input unit 108. The local output unit is configured for emitting a warning locally, when an undesirable condition relating to the user's absence or presence is detected. The local input unit is configured for enabling the user or anyone nearby to turn off the warning. Optionally, the remote system 112 is configured for sending the warning to one or more predefined persons, to inform them of the undesirable condition.

In some embodiments of the present invention, the remote system 112 is accessible to medical personnel to analyze conditions of the user, such as frequent sleep interruptions or rapid weight gain. These conditions may be indicative of heart failure, as will be described below.

In some embodiments of the present invention, the control unit analyzes the data indicative of the user's frequency of sleep interruptions and/or rapid gain weight. If the control unit determines that the frequency of sleep interruptions is too high and/or if the person's weight gain is too rapid, according to predetermined thresholds, a notification is sent via the communication unit 110 to a remote system accessible to medical personnel. Optionally, a warning is also emitted by the local output unit to inform the person of a health-related risk.

In some embodiments of the present invention, the pressure pad 102 is configured for being located under the user's mattress, and includes a varying resistance conductive material. This material is electrically conductive, like a wire, but has a resistance which decreases as pressure is applied. This allows for a resistance measuring circuit, such as a voltage divider, to be used with an Analog to Digital Converter (ADC) of a micro controller (MCU) to obtain weight measurements. In some embodiments of the present invention, the variable resistance material of the present invention may include one or more of a conductive film (e.g., a film called Velostat and produced by 3M, or any similar material), conductive foam, strain gauges which generate varying resistance when deformed, and conductive ink. Optionally, the pad is integral with a mattress/cushion, such the pressure sensitive part is a sheet or layer of the mattress or cushion.

Figure 2:
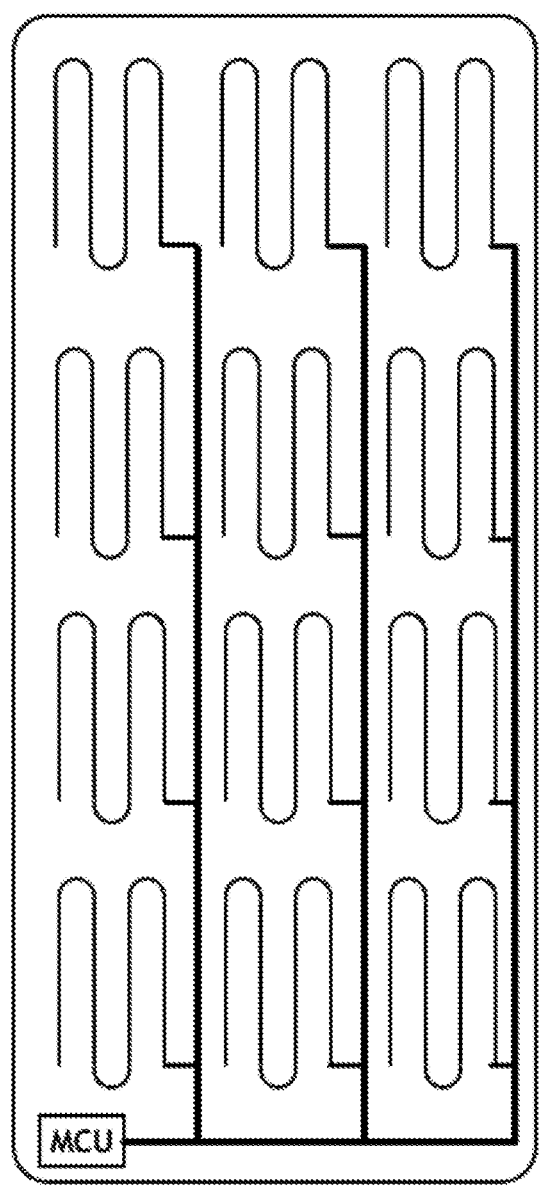
FIG. 2 is a schematic drawing illustrating a zone of the analog pressure pad of FIG. 1, or a pressure pad according to FIG. 1 that is not divided in zones, according to some embodiments of the present invention.

In an embodiment of the present invention, the analog pad 102 is divided up into zones, which in effect act like many little analog pads in a grid pattern covering the surface area of the pad. Each zone is attached to a separate ADC on the micro controller and measured independently allowing for software to determine specifically where on the pad pressure is, how much pressure is present, and as the user moves, how the pressure changes from zone to zone. FIG. 2 shows a zone of the analog pressure pad 102, or a pressure pad 102 that is not divided in zones.

The relevance of detecting position and movement is that nursing staff can be alerted when a person is in a position for too long, thus leading to possible decubitus ulcers. Moreover, caretakers can be alerted at an earlier moment the user reaches the side of the bed, in order to exit the bed. A local alert may be emitted if a user who is not supposed to leave the bed is at the edge of the bed.

Individual signals are transmitted from each pad to the control unit 110 before processing the signal in a CPU (which may be in the control unit 110 or in the remote system 112), comparing magnitudes of changes in weight. Optionally, the signals are amplified before being received by the control unit 110. Some embodiments of the present invention relate to techniques for determining when the user is starting to leave a bed, departs from bed, when the user has been in place for too long a period, and optionally, evidence of changes in a person's body weight from day to day (of diagnostic value for several conditions including congestive heart failure). Relative weight measurements could be used to detect weight gain or loss of the user over time and possibly, if calibrated correctly, supply an actual weight measurement (pounds, kilograms, etc). Historical relative weight measurements could also aid in the detection of pets that might jump into bed, such as a dog, which might otherwise have triggered an alarm in basic pressure pad.

Figure 3:
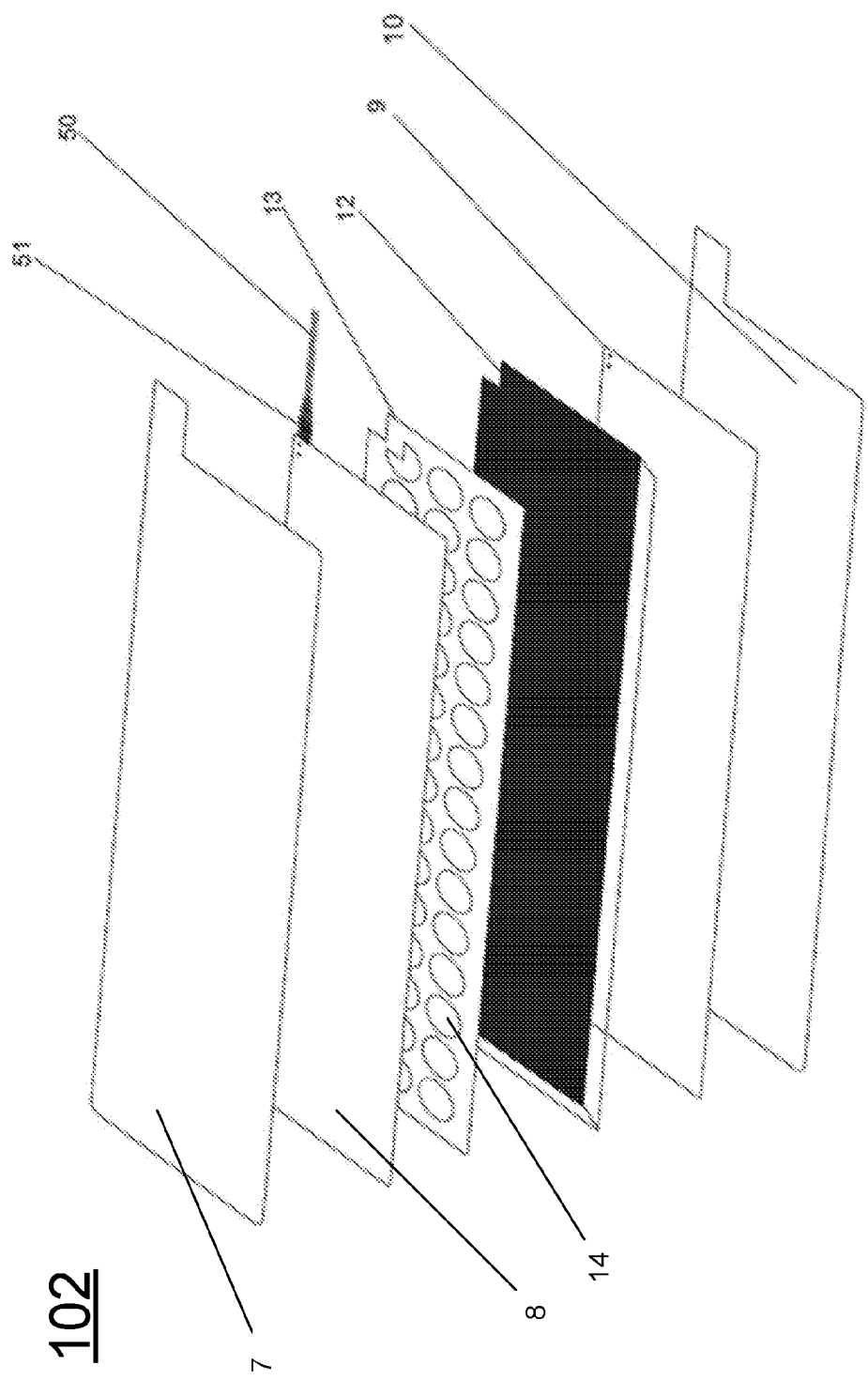
FIGS. 3 and 4 are schematic drawing illustrating an example of the structure of the pressure pad of FIG. 1 or of a zone of a pressure pad of FIG. 1, according to some embodiments of the present invention.
Figure 4:
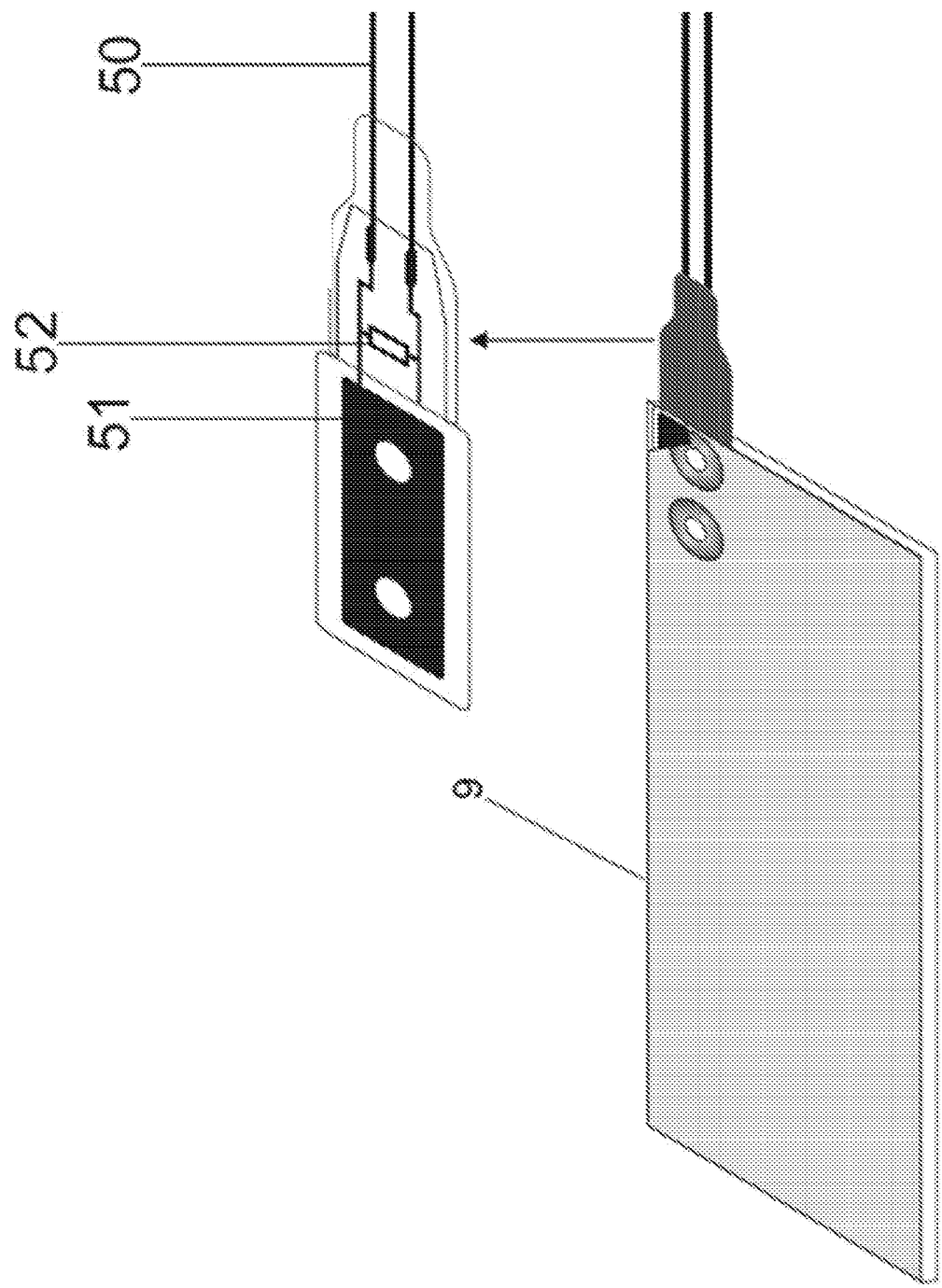

FIGS. 3 and 4 are schematic drawing illustrating an example of the structure of the pressure pad of FIG. 1 or of a zone of a pressure pad of FIG. 1, according to some embodiments of the present invention.

The pad 102 relies on an electrical circuit having pressure-sensitive resistance. The pad 102 includes two electrically conductive layers 8 and 9 (e.g., Aluminum foil PET Mylar) separated by a non-conductive layer 13 (e.g. Mylar with die cuts) and a layer of conductive foam 12. Optionally the pad 102 includes a sheath (layers 7 and 10) that contains and seals the conductive layers 8 and 9, the non-conductive layer 13, and the conductive foam 12. Optionally the sheath is an RF-welded vinyl cover. Optionally the pad 102 is fully sealed and water proof.

Electrical wires 50 are connected to each of the electrically conductive layers, and run to a circuit board 51 that connects to the micro-controller unit (MCU) which may be part of the control unit 104 of FIG. 1, or may be in communication with the control unit 104 of FIG. 1. In some embodiments of the present invention, a limitation resistor 52 is connected to circuit board and is parallel to each of the electrically conductive layers. The apparatus which includes the conductive layers, non-conductive layer, and foam layer operates as a pressure-sensitive resistor which is in parallel with the limitation resistor 52.

Optionally, the output of MCU runs to a modular connector that connects to the fall alarm.

The upper conductive layer 8 and upper face of conductive foam 12 are separated by the non-conductive layer 13. The lower conductive layer 9 is in contact with the lower face of conductive foam 12.

When no pressure is applied on the pad 102 or if the weight is lower than a certain threshold pressure, the upper conductive layer 8 and the upper face of conductive foam 12 are still separated by the non-conductive layer. The resistance present between the conductive layer 8 and 9 is very high or approaches infinity.

The output resistance $R_{OUT}$ of the pad is equal to:

$$R_{OUT} = (1/R_{VAR} + 1/R_{LIM})^{-1}$$

where, $R_{VAR}$ is the variable resistance between the conductive layers 8 and 9, while $R_{LIM}$ is the resistance of the limitation resistor 52.

Thus, when the pressure applied to the pad is lower than a certain pressure, $R_{OUT}$ is equal to value of limitation resister.

When weight/pressure present on the pad increases, the upper conductive layer 8 is compressed, allowing the upper conductive layer 8 and upper face of conductive foam 12 to make contact via the holes 14 in the non-conductive layer 13. The increased weight/pressure also compresses the conductive foam. As the conductive foam is sandwiched between two conductive layers, the resistance of conductive foam 12 between two conductive layers decreases. As the weight/pressure on the sensor pad increases more, the conductive foam is compressed more and causes the resistance of conductive foam 12 to decrease more, therefore decreasing the resistance $R_{VAR}$ between the two conductive layers 8 and 9.

As $R_{VAR}$ decreases, the output resistance of the pad, $R_{OUT}$ decreases as well. When weight/pressure on the pad decreases, the conductive foam recovers its original shape the resistance of the foam increases, thereby increasing the resistance $R_{VAR}$ between the conductive layers 8 and 9. Therefore, $R_{OUT}$ increases as well.

When the weight/pressure is removed from the pad, the upper conductive layer 8 and upper face of conductive foam 12 are separated by the non-conductive layer 13. $R_{VAR}$ therefore rises toward infinity, and $R_{OUT}$ is equal to value of limitation resister. By tracking $R_{OUT}$, $R_{VAR}$ can be calculated, and the pressure on the pad can be determined.

FIGS. 5 and 6 are schematic drawings of an electrical circuit which includes the pad of FIGS. 3 and 4, according to some embodiments of the present invention;

The circuit includes the variable resistor $R_{VAR}$ of the pad as described above, and the limiting resistor $R_{LIM}$, a power source PWR, and a reading point at which $V_{OUT}$ is read.

In the example of FIG. 5, there is no pressure on the pad, so $R_{VAR}$ is very high (e.g. 100 MΩ), compared to the resistance of $R_{LIM}$ (for example, 10 kΩ). In this example, $V_{OUT}$ will be about the same as the voltage provided by the power source (e.g., 5V).

In the example of FIG. 6, there is a high pressure on the pad, so $R_{VAR}$ is very low (e.g. 1Ω), compared to the resistance of $R_{LIM}$ (for example, 10 kΩ). In this example, $V_{OUT}$ will be about 499.95 µΩ, which is much lower that the voltage provided by the pow source (e.g., 5V) and approaches 0.

In some embodiments of the present invention, the pad does not include the non-conductive layer. This pad uses more power, but still operates correctly.

In some embodiments of the present invention, the micro controller which reads the zones and calculates the in-bed/out-of-bed determination, is separate from the control unit. This places the micro controller within the pad, on the cord for the pad, at the connector for the pad, or as an adapter which the pad plugs into or connects to wirelessly. This allows for a simple monitor with limited processing capabilities to work with the pad.

Figure 7:
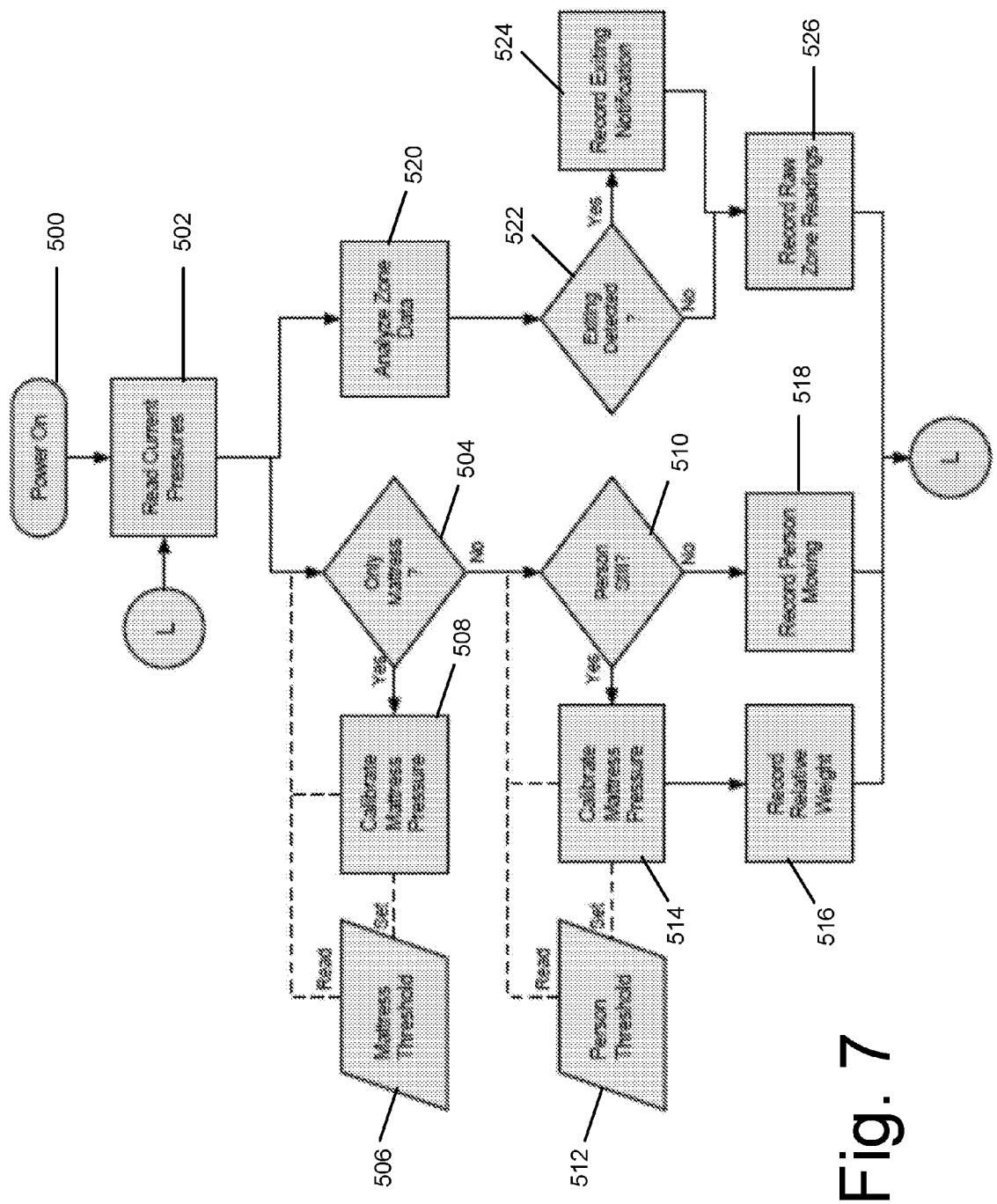
FIG. 7 is a flowchart illustrating a method used by the control unit of FIG. 1 for processing data received from the analog pressure pad.

FIG. 7 is a flowchart illustrating a method used by the control unit of FIG. 1 for processing data received from the analog pressure pad described above. It should be noted that any pressure pad may be used, in which variable resistance of the pad or its sections relates to the pressure applied on the pad or its sections. The left branch of the flowchart relates to processing analysis of the data taken by all the zones of the pressure pad. The right branch of the flowchart relates to separately analyzing data from each zone of the pressure pad.

At 500, the control unit is turned on. At 502, data indicative of pressure(s) is read from the analog pressure pad.

At 504, a check is made to determine if only the mattress is present. When no weight is applied, the resistance through the pad is very high and approaches infinite. Without the weight of a mattress, the resistance of the pad becomes very high and causes Vout is to be very close to the input voltage. Thus, when Vout is close to the input voltage, it can be assumed that no mattress is present. If this is the case, the pressure readings due to the mattress' presence are stored. A mattress threshold is set at 506 and the control unit is calibrated accordingly at 508. There are two methods in which the mattress weight can be calibrated. In the first method, a reset button or reset mechanism can be used by a staff member when the pad is first placed under a mattress, to force an immediate recalibration by zeroing out the currently applied weight. In the second method, the calibration occurs automatically via the method of FIG. 8 after the first person uses the mattress with the pad installed.

If a person is on the mattress, a check is made to determine whether the person is still at 510. If this is the case, the pressure readings due to the presence of the mattress and the person are stored. A person's threshold is set at 512 and the control unit is calibrated accordingly at 514. Since the pressure due to the mattress is known, a relative weight of the person can be determined by comparing the pressure due to the presence of the mattress and the pressure due to the presence of the mattress and the person at 516.

If the person is not still, the control unit records that the person is moving at 518. Movement of the person can be detected when a number of readings taken at predetermined intervals (e.g., 4 readings at intervals of 0.5 s) vary substantially in relation to each other. If the variance of the readings is under a predetermined threshold, it is determined that the person is still.

On the right branch of the flowchart, data from each zone of the pressure pad is processed separately at 520, and a check is made to determine whether the person is exiting the bed at 522. If this analysis determines that the person is exiting from the bed, an exiting notification is recorded at 524, and optionally a warning is issued. If exiting is not detected, the raw zone readings are recorded for later analysis at 526.

In some embodiments of the present invention, the apparatus 100 of FIG. 1 is configured for helping diagnose a health condition of the user. In a non-limiting example, nocturnal polyuria and rapid weight gain may be diagnosed by using data from the pressure pad.

Nocturnal polyuria is a condition in which a person wakes up frequently during the night to urinate. A healthy person should be able to sleep six to eight hours during the night without having to get up to go to the bathroom. People suffering from nocturnal polyuria wake up more than once a night to urinate. This can cause disruptions in a normal sleep cycle. Causes of nocturnal polyuria may include congestive heart failure.

By utilizing the apparatus according to FIG. 1 (with a regular or an analog pressure pad) to keep a nocturnal diary, it is possible to reliably track how many times the user rises during the night. While the apparatus may not detect whether the user has woken up to use the bathroom, data relating to frequent interruptions in the user's sleep may be an indicator that something might be wrong.

Rapid weight gain is commonly experienced by people suffering from heart failure. In fact, if a person's heart failure is causing fluid accumulation, the person will gain weight in a short time period.

People who are at risk for heart failure should weight themselves every day at the same time, and to report to medical personnel, if the weight increases quickly (for example, by more than 2 kilograms in 3 days, or by more than 3 pounds in 3 days).

By using the apparatus of FIG. 1, the relative weight of the user each night is recorded while they are asleep. The measurements are relative weight, but since we are interested in weight gain these relative measurements can be compared to each other from day to day to detect rapid weight changes. This removes the element of forgetfulness on the part of the user to weigh himself or herself daily, and negates observation bias by dealing with discrete recorded measurements instead of the user's memory of past weights.

Figure 8:
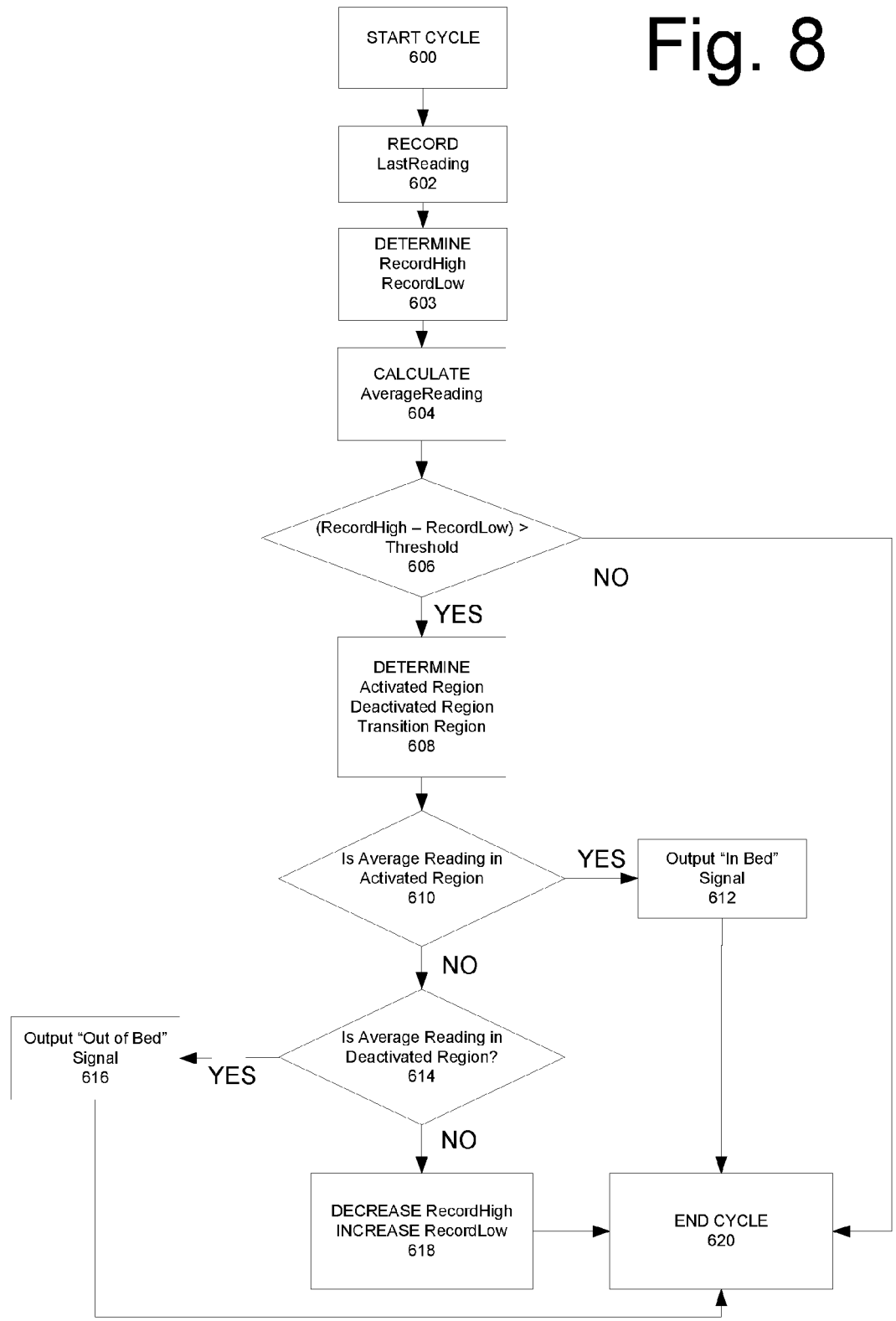
FIG. 8 is a flowchart illustrating a method of some embodiments of the present invention, for dynamic calibration of a pressure sensitive pad according to FIG. 1, to any mattress and/or person.

FIG. 8 is a flowchart 600, illustrating a method of some embodiments of the present invention, for dynamic calibration of a pressure sensitive pad according to FIG. 1, to any mattress and/or person. The method may be implemented by the control unit of FIG. 1.

At 600, a new cycle is started. At 602, a resistance reading from the pad is recorded by the control unit. The recorded reading is called LastReading. At 603, LastReading is compared to previous readings, to determine RecordHigh and RecordLow, which are respectively the highest and lowest resistances recorded over a predetermined time period.

At 604, an average reading is calculated. The average reading may be an average of the readings recorded over a certain time period, or may be weighted average, in which the current LastReading weighs more than previous readings.

At 606, a check is made to determine whether a difference between the RecordHigh and RecordLow is greater than a certain threshold. At this point the control unit needs to make a decision if it has gathered enough data in order to execute the remaining logic or if it needs to go back to sleep. This is required because a newly initialized control unit will have a RecordHigh=RecordLow=AverageReading and if they aren't exactly equal they will be very close in value which creates an error condition. In this state a large enough range of pressures have not been recorded. Therefore, an in bed (person on mattress) or out of bed (person off mattress) condition cannot be determined. In some embodiments of the present invention, the threshold value is hardcoded and depends on the responsiveness of the pad material used.

If the difference between RecordHigh and RecordLow is smaller than the threshold, the cycle is ended at 620. If the difference between RecordHigh and RecordLow is larger than the threshold, three ranges or regions are determined at 608: the activated region, the deactivated region, and the transition region.

The activated region includes a range of values, such that if the last reading or average reading is within the activated region, it is determined that the person is in bed. The lowest value of the activated region is RecordLow (as low resistance corresponds to high pressure on the pad). The highest value of the activated region is a first function of RecordHigh and RecordLow. For example, the highest value of the activated region may be:

RecordLow+$f_1$(RecordHigh, RecordLow), where $f_1$ is a first function.

The deactivated region includes a range of values, such that if the last reading or average reading is within the deactivated region, it is determined that the person is out bed. The highest value of the deactivated region is RecordHigh (as high resistance corresponds to low pressure on the pad). The lowest value of the activated region is a second function of RecordHigh and RecordLow. For example, the highest value of the activated region may be:

RecordHigh−$f_2$(RecordHigh, RecordLow), where $f_2$ is a second function.

The transitional region corresponds to a range of values higher than the highest value of the activated region and lower than the lowest value of the deactivated region.

At 610, a check is made to determine whether the AverageReading is within the activated region. Alternatively, the check of 610 is made to determine whether the LastReading is within the activated region. If the check is positive, an "In Bed" signal is output at 612. This signal may be sent to a remote station, or used by the control unit to determine whether the fact that the person is in bed is a desirable or undesirable condition, and act accordingly.

If the check of 610 is negative, another check is made at 614 to determine whether the AverageReading is within the deactivated region. Alternatively, the check of 614 is made to determine whether the LastReading is within the deactivated region. If the check of 614 is positive, an "Out of Bed" signal is output at 616. This signal may be sent to a remote station, or used by the control unit to determine whether the fact that the person is out bed is a desirable or undesirable condition, and act accordingly.

In an ideal situation the above stated steps would be sufficient for full pad operation. If this was the case, recordHigh would be the tare weight of the mattress and recordLow would represent the weight of the patient plus mattress. During real world usage, events occur which push the recordHigh and recordLow briefly to extremes which do not represent their intended representations. This could be as simple as a staff member remaking a bed who accidentally leans too hard on the mattress while tucking in the far corner. If these outliers were not accounted for the pad would function for a time, but slowly become less and less reliable until it stops seeing the patient all together.

In order to rectify this, the transition region calculated earlier is used to adjust the record values. Thus, if the check of 614 is negative, then the AverageReading (alternatively, the LastRading) is in the transitional zone. Thus, for every wake cycle in which the averageReading (alternatively, the LastRading) is within the transition region the RecordHigh is decreased by a first amount and the RecordLow is increased by a second amount at 618. The first and second amounts may be calculated by third and fourth functions, each function taking into account both RecordHigh and RecordLow.

The increase or RecordLow and the decrease or RecordHigh decreases the distance between these values. If a much lower high or much high low is observed than previously these record values will start to converge until the AverageReading (alternatively, LastReading) is once again within either the Activated or Deactivated region. In some cases this convergence may take a minute if sampling occurs every 0.5 s, but it prevents the staff from needing to manually intervene in the calibration process.

At 620, the cycle ends. A new cycle begins according to a predetermined sampling time. The time interval between cycles may be 1 seconds, 100 milliseconds, 10 milliseconds, or any other value that is deemed desirable.

The method of FIG. 6 can be used to dynamically calibrate a pad to new conditions, such as a new mattress and a new person having a different weight. Depending on the sampling time and on the period over which the AverageReading, RecordHigh, and RecordLow are determined, and on the formula used for calculating AverageReading, a pad can be calibrated to new conditions within a minute when sampling occurs every 0.5 s. Alternatively, a pad can be initialized to start a new calibration via the control unit each time the pad is transferred to anew mattress or a new person.

Figure 9:
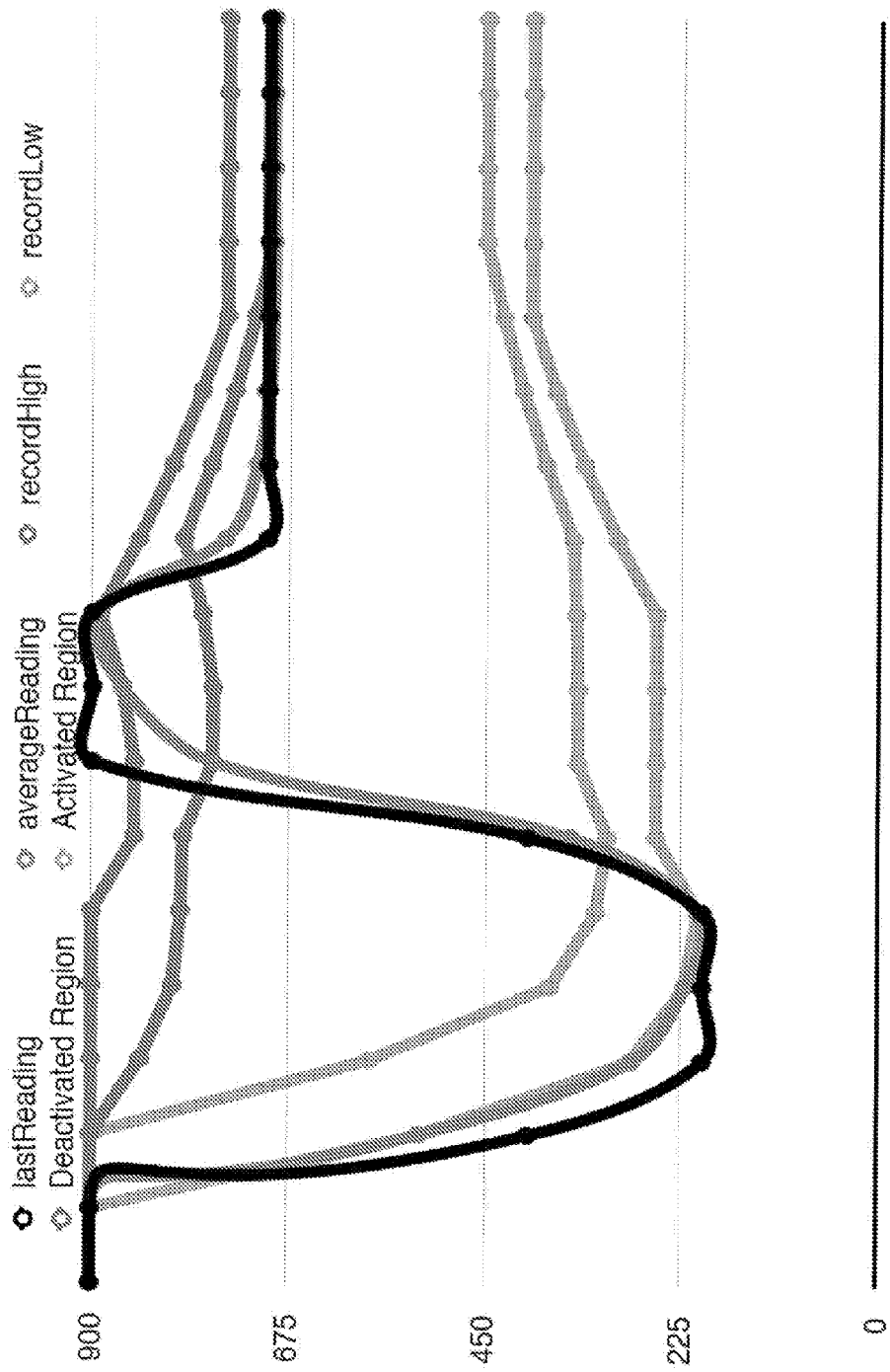
FIG. 9 is a resistance vs. time graph, illustrating the calibration of a pad of FIG. 1 over time, according to the method of FIG. 8.

FIG. 9 is a resistance vs. time graph, illustrating the calibration of a pad of FIG. 1 over time, according to the method of FIG. 8. The green lines represent the Activated region while the red lines represent the Deactivated region. As the LastReading (black) changes the AverageReading (blue) follows it, but slightly lagging behind. In the last half of the graph the LastReading drops to 700 which is in the Transition Region. At this point the red and green regions begin to converge until the red region captures the current AverageReading. According to some embodiments of the present invention, the control unit of FIG. 1 keeps track of the relative of weight of the person to be monitored when the person is on the bed. The relative weight eight is relative because it depends on the weight and structure of the mattress and on the weight of the person. Readings from the pad would differ even if the same person were to lie on two different mattresses.

In the simplest embodiment of a system, measuring the relative weight the pad of FIG. 1 includes one single zone. In this embodiment, the entire weight of the individual is applied to the single sensor zone. This weight is distributed unevenly based on the position and stance of the monitored person, but the unevenness is not detected since all the pressure measured by the pad is all contained within a single zone.

In a slightly more complex embodiment of a system, measuring the relative weight the pad of FIG. 1 includes two sensor zones, in which the dividing line runs through the center of the pad. If the person's center of mass is along the dividing line, the same amount of pressure is being applied to the pad as a whole, but now half of that pressure resides on each zone. All other things remaining the same, the voltage drop across each zone is reduced by a certain coefficient as the pressure resistance of each zone is doubled compared to the single zone example. The coefficient depends on the structure of the pad, on the structures and weight of the mattress, and on the stance and weight of the person.

This example can be extended out again by dividing each of those zones in half but this time divided parallel to the first division. This provides four zones extending across a bed. However, the pressure is no longer equally distributed among the zones. For example, ⅕ of the pressure may be on the outer zones and the remaining ⅘ on the central zones. The voltage drops (directly proportional to the resistances) at each zone change according to the ratio of the total pressure applied on the zone. This allows for the addition of the voltage drops for a multi-zone pad to simulate a single zone for presence. In one embodiment, total pressure=f(Vout 1)+f(Vout 2)+f(Vout 3)+ . . . +f(Vout n) for n zones. For example, f=Vout/(Vcc/1024). In another example the function f is a logarithmic function and the total pressure is related logarithmically to the output voltage. For the single zone pad, total pressure=f(Vout). The multi-zone pad, however, provides zone granularity to determine bed location and position. It is important to remember all of these voltage drops represent relative weights and not absolute measurements. The material and composition of the mattress will affect pressure dispersement. This means reading between mattresses cannot be compared. Multiple readings from the same mattress are comparable, and allow tracking the relative weight of the monitored person.

It should be noted that the weight distribution across the different zones allows the determination of the person's position on the mattress. For example, if most of the weight is concentrated on the outer sides of the bed for a prolonged time, there may be a chance that the person is trying to get up or is about to fall.

The other item to keep in mind is patient movement when using readings for relative weight measurements. If the patient is actively shifting or fidgeting, the kinetic energy imparted to the mattress appears as additional pressure to the sensors and therefore additional weight. To account for this, multiple measurements should be taken over several seconds for each zone and each of the zone reading should be compared to itself over that time period. If little to no fluctuation in the readings over several seconds are observed the algorithm can assume the individual is lying still. Otherwise the system should delay several minutes before reattempting another relative weight measurement. On the other hand, a failed relative weight measurement is also an active individual measurement if presence has already been determined. A failed weight measurement in this case is due to the patient moving too much. This has the benefit of determining the monitored person is moving, which can be used as an indication of restlessness, shifting, or the possibility of waking from sleep, if it is preceded by an extended period of stillness in the middle of the night.

In one example, the relative weight is determined by the sum of the voltage drops from all zones. f=pressure reading=Vout/(Vcc/1024) In some embodiments of the present invention, the micro controller (MCU) of each zone reads each zone as a 10 bit value between the reference voltage (for example, 5V) and ground. Optionally, the micro controllers are configured to create an even more fine grained reading (for example 12 bits and 14 bits). At a 10 bit resolution, the MCU is able to measure in approximately 4.88 mV increments of the maximum voltage drop, where the maximum voltage drop is 5V. The addition of these four zones provides a relative range between 4092 increments (of the maximal voltage drop) with no pressure (resistance is infinite, thus voltage drop is maximal) and theoretically 0 increments at an infinite pressure (at infinite pressure, the resistance is 0, so the voltage drop is 0).

Figure 10:
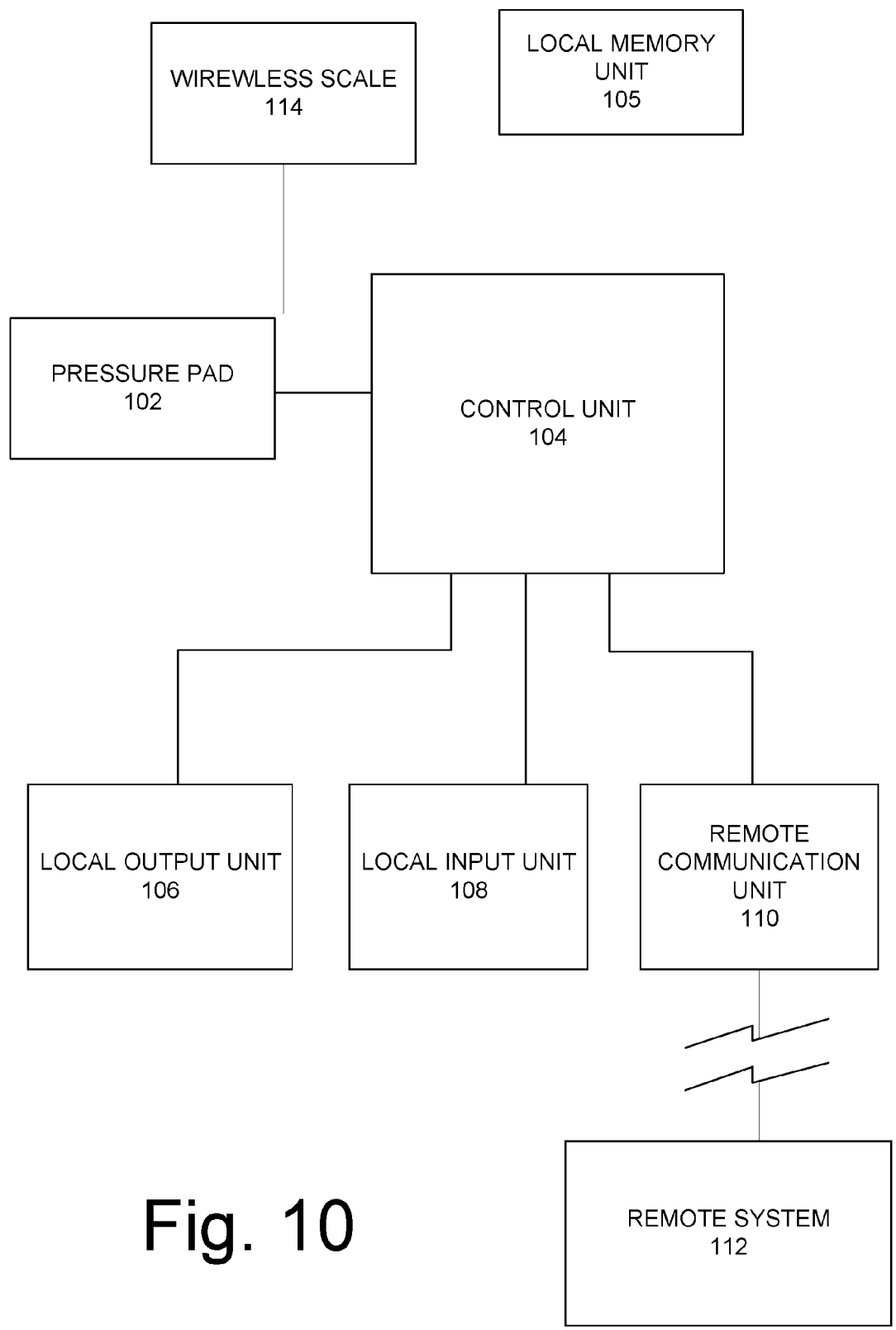
FIG. 10 is a block diagram illustrating a system of the present invention, in which the control unit is in communication with a wireless scale.

FIG. 10 is a block diagram illustrating a system of the present invention, in which the control unit is in communication with a wireless scale. The apparatus of FIG. 10 is similar to the apparatus of FIG. 1. However, in FIG. 8, a wireless scale 114 is in communication with the control unit. The wireless scale records the weight of the person, and sends data indicative of the person's weight to the control unit. The control unit records the weight and the time of the weighing. The data is either analyzed locally and sent to medical personnel only if a threshold is reached, or is directly sent to medical personnel, as described above. The weight data may be able indicate whether the user is at risk for heart failure. The calibrated weight from a scale can be used by the control unit to assist in calibrating the pressure pad's relative weights into absolute weights (pounds or kilograms).

It should be noted that the inventors have found that different variably resistive materials perform differently under a mattress. A first material (conductive film) appears to be very reliable for "in bed" and "out of bed" detection, while a second material (conductive foam) is more reliable at providing a relative weight once a user is in bed and lying still. Therefore, in some embodiments of the present invention, the analog pad with includes two types of variably resistive materials in communication with the control unit. Data from the first material is used for in bed and movement detection. Once the movement stills data from the second material is sampled for determining weights. As soon as movement is detected again, the control unit analyzes data from the first material again.

What is claimed is:

1. A pressure sensitive pad, generally planar in shape for placement underneath a mattress or cushion, capable of outputting a spectrum of signals depending on the pressure applied on the pad, the pressure sensitive pad being configured for being connected to a control unit, such that the control unit is configured for processing the spectrum of signals received from the pad, and the control unit is operable to:
   (a) automatically calibrate the control unit to detect absence and presence of a person for a range of mattress types and weights and person weights; and
   (b) determine a relative weight of the person while the person is on the mattress.

2. The pressure sensitive pad of claim 1 configured for not deforming the mattress or cushion.

3. The pressure sensitive pad of claim 1, comprising at least one of: a conductive film; a conductive foam; a conductive ink; and a strain gauge.

4. The pressure sensitive pad of claim 1, comprising a plurality of sensitive zones, each zone being connected to a respective controller, configured to measure the pressure on each zone.

5. The pressure sensitive pad of claim 1, comprising:
   two electrically conductive layers;
   a variable conductive layer between the two conductive layers, configured such that a resistance of the variable conductive layer decreases when pressure is applied on the variable conductive layer and the variable conductive layer is compressed;
   wherein the two electrically conductive layers are separated by the variable conductive layer, such that the electrical resistance between the two conducting layers decreases as pressure is applied to the pad, by way of increasing electrical conductivity between the two conducting layers as mechanical pressure increases on the pad and the variable conductive layer is compressed.

6. The pressure sensitive pad of claim 5, wherein the variable conductive layer is a conductive foam layer.

7. The pressure sensitive pad of claim 6, comprising a non-conductive layer comprising a plurality of holes, disposed between a first of the two electrically conductive layers and the conductive foam layer;
   wherein pressure applied to the pad increases contact between the first conductive layer and the conductive foam, thereby easing electrical conductivity between the two electrically conductive layers.

8. The pressure sensitive pad of claim 5, comprising a controller connected to the two conducting layers and configured to input a signal that passes through the two electrically conductive layers to read an output signal resulting from the input signal passing through the electrically conductive layers; and two sheath layers that contain and protect the electrically conductive layers.

9. A system for detecting weight of a person or weight changes over time or movements of a person on a mattress, comprising:
   an analog variable pressure sensitive pad configured for placement under a mattress; and
   a control unit configured for processing data received from the pad, and the control unit operable to:
   (a) automatically calibrate the system to detect absence and presence of a person for a range of mattress types and mattress weights and person weights; and
   (b) determine a relative weight of the person while the person is on the mattress.

10. The system of claim 9, wherein the control unit is operable to:
    (c) send processed data to a remote system;
    (d) emit an alarm if an undesirable situation concerning the person's presence/absence occurs; and
    (e) stop the alarm if a certain input is received.

11. The system of claim 10 comprising a local output unit configured for emitting an alarm in response to an undesirable condition of the person occurring based on information from the pad.

12. The system of claim 10, further comprising a local input configured for receiving a termination signal, communicated to the control unit, whereby the controller is configured to terminate an emitted alarm.

13. The system of claim 10, comprising a remote communication unit configured to transmit data processed by the control unit to a remote system.

14. The system of claim 13, wherein the data transmitted is alert data.

15. The system of claim 13, wherein the data is weight data.

16. The system of claim 9, wherein the control unit is configured to determine the relative weight of the person, by calibrating the system to detect the person's weight when the pressure sensitive pad is placed beneath the mattress of an unknown weight and the person is on the mattress, the calibrating comprising:
    i) measuring a record high, a record low, a last reading and an average reading from the pad;
    ii) if a difference between the record high and the record low is smaller than a threshold, gathering more data until threshold is passed;
    iii) if the difference is greater than the threshold:
      iii-a) determining a deactivated zone, wherein the deactivated zone is a range of values from the high to a value that is a function of the low and high;
      iii-b) determining an activated zone, wherein the activated zone is a range of values from the low to a value that is a second function of the low and high; and
      iii-c) determining a transition zone, wherein the transition zone is range between the highest value of the activated zone and the lowest of deactivated zone;
    iv) if the average value is in the transitioning zone, then performing an iterative process of lowering the record high by a second amount that is a third function of the previous record highs and lows and increasing the record low by a third amount that is a fourth function of the previous record highs and lows, until the last reading is out of the transitioning zone.

17. A method for calibrating a variable pressure sensitive pad to detect a person's weight, when the pressure sensitive pad is placed beneath a mattress of an unknown weight and the person is on the mattress, the calibration comprising:
    a) placing the pressure variable pressure sensitive pad undress a mattress;
    b) measuring a record high, a record low, a last reading and an average reading from the pad;
    c) if a difference between the record high and the record low is smaller than a threshold, gathering more data until threshold is passed;
    d) if the difference is greater than the threshold:
      i) determining a deactivated zone, wherein the deactivated zone is a range of values from the high to a value that is a function of the low and high;

ii) determining an activated zone, wherein the activated zone is a range of values from the low to a value that is a second function of the low and high; and iii) determining a transition zone, wherein the transition zone is range between the highest value of the activated zone and the lowest of deactivated zone;

e) if the average value is in the transitioning zone, then performing an iterative process of lowering the record high by a second amount that is a third function of the previous record highs and lows and increasing the record low by a third amount that is a fourth function of the previous record highs and lows, until the last reading is out of the transitioning zone.

18. The method of claim 17, wherein the second amount and the third amount are equal to each other.

* * * * *